United States Patent [19]

Polak et al.

[11] Patent Number: 4,689,122

[45] Date of Patent: * Aug. 25, 1987

[54] GAS DETECTION APPARATUS AND METHOD WITH NOVEL ELECTROLYTE MEMBRANE

[75] Inventors: Anthony J. Polak, Lake Zurich; Allyson J. Beuhler, Indian Head Park, both of Ill.

[73] Assignee: UOP Inc., Des Plaines, Ill.

[*] Notice: The portion of the term of this patent subsequent to Feb. 19, 2002 has been disclaimed.

[21] Appl. No.: 854,443

[22] Filed: Apr. 21, 1986

Related U.S. Application Data

[63] Continuation-in-part of Ser. No. 566,923, Dec. 29, 1983, abandoned.

[51] Int. Cl.$^4$ ............................................. G01N 27/58
[52] U.S. Cl. ..................... 204/1 T; 204/421; 204/426; 204/427
[58] Field of Search ............... 204/1 T, 1 B, 1 F, 1 S, 204/421, 424, 426, 427; 429/33, 192

[56] References Cited

U.S. PATENT DOCUMENTS

| | | | |
|---|---|---|---|
| 3,265,536 | 8/1966 | Miller et al. | 136/86 |
| 3,276,910 | 10/1966 | Grasselli et al. | 136/86 |
| 3,727,058 | 4/1973 | Schrey | 204/424 X |
| 4,024,036 | 5/1977 | Nakamura et al. | 204/129 |
| 4,179,491 | 12/1979 | Howe et al. | 204/1 T X |
| 4,306,774 | 12/1981 | Nicholson | 350/357 |
| 4,324,760 | 4/1982 | Harris | 422/98 |
| 4,324,761 | 4/1982 | Harris | 422/98 |
| 4,373,375 | 2/1983 | Terhune et al. | 73/19 |
| 4,500,667 | 2/1985 | Polak et al. | 524/406 |
| 4,560,444 | 12/1985 | Polak et al. | 204/427 X |

OTHER PUBLICATIONS

Lundsgaard et al., "A Novel Hydrogen ... Phosphate", Solid State Ionics 7 (1982) 53-56.
Platinum Metal Review, Jan. 1983, vol. 27, No. 1, p. 8, "Hydrogen Detector Uses Silver-Palladium Probe".
Instrumentation Tech., Aug. 1972, pp. 29-31, "A Thin-Film Hydrogen Sensor", by MacIntyre et al.

Primary Examiner—John F. Niebling
Assistant Examiner—Nam X. Nguyen
Attorney, Agent, or Firm—Thomas K. McBride; John F. Spears, Jr.; Richard J. Cordovano

[57] ABSTRACT

Apparatus and method for detecting and measuring hydrogen and gaseous compounds capable of dissociating into or combining with hydrogen ions using a solid electrolyte concentration cell. A novel solid electrolyte membrane is used which comprises an organic polymer-inorganic compound blend prepared by admixing an organic polymer such as poly(vinyl alcohol) with a heteropoly acid or salt thereof such as dodecamolybdophosphoric acid in a mutually miscible solvent.

18 Claims, 4 Drawing Figures

GAS DETECTION APPARATUS AND METHOD WITH NOVEL ELECTROLYTE MEMBRANE

This is a continuation-in-part of co-pending application Ser. No. 566,923, filed Dec. 29, 1983, now abandoned.

BACKGROUND OF THE INVENTION

This invention relates to electrochemical measurement and detection. More specifically, it relates to the use of a novel solid electrolyte and a catalyst in detecting the presence of hydrogen or gases capable of dissociating to yield or combining with hydrogen ions, including oxygen, and measuring the quantity present.

The use of solid electrolyte sensors for detecting oxygen, particularly in automotive exhaust gases, is well known. The present invention utilizes similar basic principles for detection of certain gases. The Nernst equation describes the behavior of sensing devices using solid electrolytes. When two media with different partial pressures, $P_1$ and $P_2$, of a particular substance present in both media are separated by a solid electrolyte (ionic conductor) and conducting electrodes are attached to both sides of the ionic conductor, an EMF is generated which is related to the partial pressures as follows:

$$EMF = E_o + \frac{RT}{nF} \ln \frac{P_2}{P_1},$$

where R is the gas constant, T is absolute temperature, F is the Faraday constant, $E_o$ is the standard oxidation-reduction potential difference, EMF is electromotive force, and n is the number of electrons per molecule of product from the overall cell reaction. If the system described by the above equation behaves non-ideally, the partial pressures must be replaced by fugacities. Another factor which may need to be considered in regard to a particular system is the rate of dissociation to form the ions which pass through the solid electrolyte. This may be a limiting factor to the transfer of ions through the electrolyte. The rate of dissociation can be calculated by means of the equilibrium constant for the dissociation reaction.

A novel solid electrolyte membrane is used in the present invention. We have discovered that a polymer blended membrane may be fabricated by admixing a heteropoly acid or a salt thereof with an organic polymer which is at least partially compatible with said heteropoly acid or salt to form a polymer blended composition of matter which is useful in gas detection. It was totally unexpected that a thin film membrane could be cast from such a blend to provide a membrane which would be highly selective to certain gases and therefore able to act as a proton conductor in a hydrogen detector where molecular hydrogen is converted into protons on one side of the device, transported through the membrane, and recombined as molecular hydrogen on the other side. The membrane is also useful in detection of gases capable of dissociating into or combining with hydrogen ions. For background information relating to the present invention, reference may be made to the book *Solid Electrolytes and Their Applications*, edited by Subbarao, Plenum Press, 1980.

INFORMATION DISCLOSURE

The present invention utilizes a composition of matter which is similar to the subject matter of U.S. Pat. No. 4,500,667 (Polak and Beuhler, issued Feb. 19, 1985), which was co-pending with the parent of this application.

U.S. Pat. No. 4,024,036 (Nakamura et al.) describes a proton-conducting solid member which is fabricated by compression molding of a heteropoly acid or salt thereof. Also, Nakamura indicates that a single crystal may be grown and used, but that the crystal consists of only one substance, i.e., the heteropoly acid or salt thereof. Of course, this teaching is not sufficient to lead one skilled in the art to the present invention, in which a heteropoly acid or salt thereof is combined with one of certain specified organic polymers.

In column 6 of Nakamura, a table is presented which gives the results of tests made on a compression-molded member made from a heteropoly acid in powder form and a fluorine resin in powder form, in this case ethylene tetrafluoride. The reference states, in column 6, that addition of not more than 1% by weight of a fluorine resin results in an increase in mechanical strength without entailing an appreciable decline in ionic conductivity. It can be seen from the table that adding larger amounts of fluorine resin to the heteropoly acid causes a significant loss in ionic conductivity.

There are numerous reasons why the present invention is not obvious to one skilled in the art from a consideration of Nakamura. The present invention utilizes an organic polymer chosen from a particular enumerated group. Nakamura utilizes a monomer, ethylene tetrafluoride, and states that other fluorine resins may also be used. The use of the monomer in Nakamura does not inform one skilled in the art of the particular organic polymers of the present invention. Further, the present invention uses from about 30% to about 90% of one of the particular organic polymers, whereas use of such quantities of fluorine resin in Nakamura results in unacceptable electrical properties. Since the monomer utilized by Nakamura cannot be present in large quantities without unacceptably degrading ionic conductivity, whereas the organic polymer of the present membrane is present in amounts of at least 30% by weight, it can be seen that Nakamura actually teaches away from the present invention.

It is clear to one skilled in the art who has considered the whole of the reference that Nakamura teaches addition to the heteropoly acid of a small amount of a second substance which does not chemically react with the heteropoly acid. The present invention produces a single-phase membrane: unlike Nakamura, the two substances interact chemically.

The present specification details the basis for the conclusion that the present membrane is single phase and therefore totally different from Nakamura. It is pointed out that the composition of the present invention has only a single glass transition temperature, as determined in tests using a differential scanning calorimeter. A two-phase system, or physical mixture, has two separate and distinct glass transition temperatures.

It is further pointed out in the present specification that examination of the inventive composition using infrared spectroscopy shows strong bands which indicate that there is intermolecular bonding between the heteropoly acid and the organic polymer.

Examination of the present composition with an optical microscope and with a scanning electron microscope indicates that only a single phase is present. Further indications of a single phase are a comparison of yield strength and modulus of the invention with those properties of the two components tested separately. Also, the membrane of the present invention is transparent and uniform in color. These properties all indicate a single phase.

However, it should be noted that it is not required that the present composition of matter be a single phase in order to be patentable. As stated in the present specification, it was totally unexpected that mixing a heteropoly acid or salt thereof with an organic polymer in a mutual solvent and recovering a membrane after removing the solvent would result in a proton-conducting membrane which is substantially impervious to other substances. Nakamura does not suggest such a result and does not suggest the organic polymers used in the present invention.

U.S. Pat. No. 3,276,910 (Grasselli et al.) teaches a new composition of matter. The essence of the Grasselli disclosure can be seen at column 6, line 38: "There has been provided a new material, rehydrated inorganic polymers . . . " These ion-conducting substances, which are quite different from the proton-conducting materials of the present invention, are discussed in the patent and are claimed.

There is one paragraph in Grasselli in which it is stated (line 53, column 2): "To endow these solid inorganic polymers with more flexibility, it has also been found that finely ground rehydrated inorganic polymer may be blended with an oxidation resistant organic polymer such as . . . " This is the only mention in Grasselli of blending a second substance with the Grasselli composition. The substances listed in Grasselli are not the same as the organic polymers used in the present invention.

It is improper to state that the present membrane is made obvious to one skilled in the art by the combination of Nakamura and Grasselli: the ancillary reference simply does not teach the organic polymers used in the present invention. Further, the organic polymers of Grasselli are used in a different manner.

All that Grasselli does is add to the Nakamura teaching more substances which can be utilized in the same manner as the ethylene tetrafluoride monomer of Nakamura. Just as in Nakamura, the finely ground ion-conductive substance is mixed with a substance in powder form. There is nothing in Grasselli which teaches that any organic polymer can be blended in solution with an ion-conductive substance, much less the organic polymers of the present invention. And the ion-conductive substance of the present invention is quite different from that of Grasselli.

Though there is only one paragraph in Grasselli which deals with mixing organic polymers with the different ion-conductive material, it can be seen from column 4 that the method of addition is mixing the two substances in powder form. Clearly this physical mixture of totally different compounds does not point the way toward the present invention.

U.S. Pat. No. 3,265,536 (Miller et al.) teaches an ion-conductive member which consists of cross-linked polyvinyl alcohol containing a filler substance uniformly embedded therein which is saturated with an alkali. Polyvinyl alcohol, a cross-linking agent, and solid particles of an alkali-stable filler material are added to water and a sheet is cast from the mixture and cured. The cured sheet is then soaked in an alkali solution, such as sodium hydroxide. The filler material can be virtually any alkali-stable solid substance. Possible filler materials include carbon, asbestos, and polytetrafluoroethylene.

The only similarity between Miller and the present invention is the use of one of the enumerated group of organic polymers, polyvinyl alcohol. The use of a filler material which can be an organic polymer or an organic solid or virtually any alkali-stable solid in no way informs one skilled in the art of combining a heteropoly acid or salt thereof with polyvinyl alcohol to obtain an embodiment of the present invention. Soaking the Miller membrane in a basic substance teaches away from the use of an acidic substance, as in the present invention. The cross-linking agent used to treat the polyvinyl alcohol in Miller may be a mineral acid or a compound such as glyoxal. Of course, any acidic material in the membrane is neutralized when the membrane is soaked in the basic solution.

BRIEF SUMMARY OF THE INVENTION

It is among the objects of the present invention to provide methods and apparatus of detecting hydrogen ion and therefore dissociable hydrogen compounds and of detecting compounds capable of combining with hydrogen ion in order to indicate the presence or absence of these substances and, where desired, provide quantitative information on the amount present.

The invention utilizes a concentration cell whose electrolyte is a thin film organic-inorganic membrane which conducts hydrogen ions. The membrane is mounted in a sample cell or membrane housing having a sample gas chamber and a reference gas chamber. The sample gas chamber contains the gas sample of interest, which must include a component capable of dissociating to form hydrogen ions or capable of combining with hydrogen ions. In the other chamber is a reference gas whose composition is known. The membrane must be substantially imporous so that the two gases will not mix by diffusing through it. A catalytic agent for promotion of dissociation or combination is in intimate contact with the membrane on the sample gas side. Catalytic agent is also provided in a like manner on the other side. It is not necessary that the same catalytic agent be used on both sides. Means for forming electrical contact and transferring electrons to and from an external circuit are provided on each side of the electrolyte in intimate contact with catalytic agent. The cell EMF is measured across said means and provides an indication of the presence of hydrogen or gases capable of combining with it in the sample gas and/or a quantitative measure of the amount of such which is present. The magnitude of EMF produced is generally in accordance with the parameters discussed above: the Nernst equation and, where applicable, the dissociation equilibrium constant. However, required practice in measuring concentration is to periodically calibrate the measuring apparatus by use of samples whose composition is known. Thus, exact adherence to theoretical relationships is not required of commercially used methods and apparatus. The primary commercial requirement is repeatability.

The method of the invention may be summarized as a method for detection in a gas sample of a gaseous component which is capable, in the presence of a catalytic agent, of dissociating to yield hydrogen ions or of combining with hydrogen ions, such method comprising contacting said gas sample with a first surface of a thin film organic-inorganic membrane and detecting EMF between means for forming electrical connection with two separate portions of a catalytic agent effective to promote dissociation and combination, where one portion of catalytic agent is in contact with said first surface and one portion of catalytic agent is in contact with a second surface of said membrane, which membrane isolates said gas sample from a reference gas and has said second surface exposed to the reference gas, said membrane comprising a blend of a compound selected from the group consisting of heteropoly acids and salts thereof and a polymer which is at least partially compatible with said compound.

A calculating device may be used to automatically calculate concentrations, or calculation may be accomplished manually. This device may receive input from a temperature probe, or temperature may be entered manually for use in the calculation. Temperature of the gas or gases and/or the membrane housing may be controlled at a pre-established value. The catalytic agent may be nickel, platinum, palladium, or alloys thereof. The catalytic agent may be electrically conductive. The form of the electrolyte element may require that gas which contacts it be dry or that at least one of the gases contain water vapor. Where temperature of the sample gas is too high or low for effective detection, it may be adjusted before the gas is contacted with the electrolyte element. It may be necessary to adjust the concentration, in a known manner, of sample gas contacting the membrane in order to achieve effective detection.

DETAILED DESCRIPTION OF THE INVENTION

Figure 1:
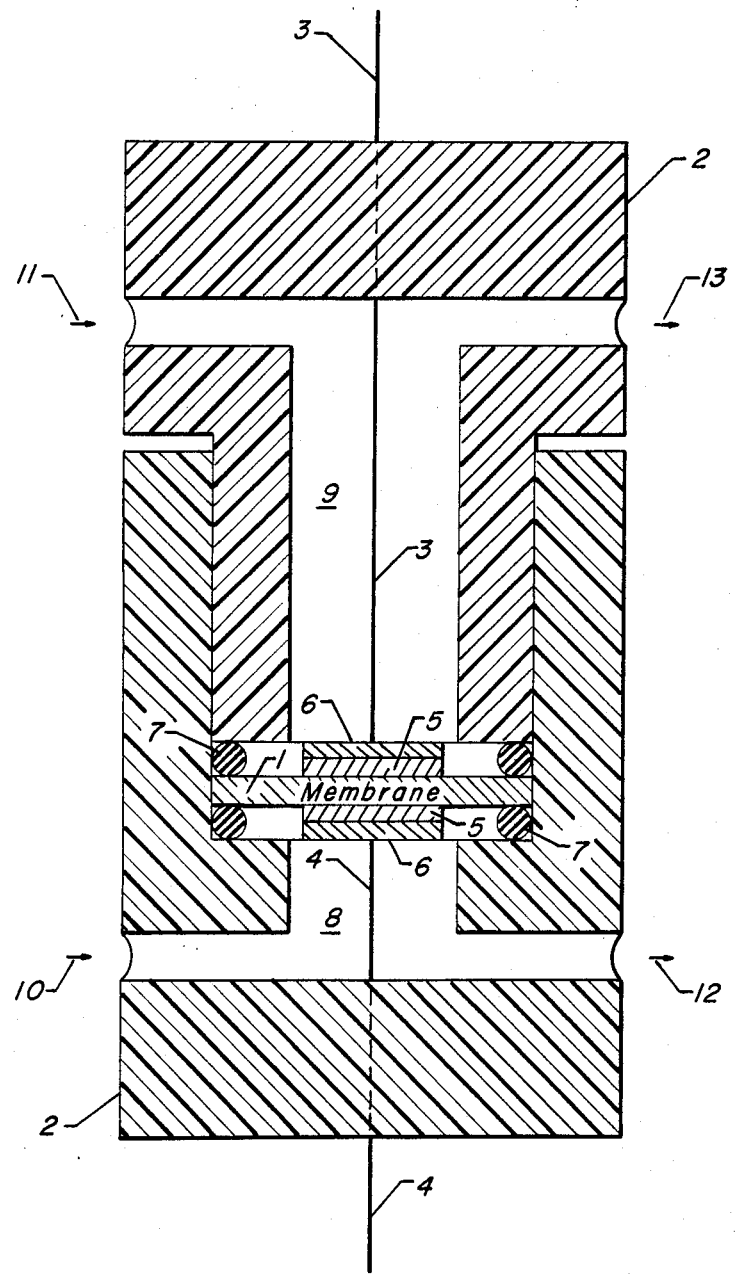
FIG. 1 is a schematic representation, in cross-section, of a test sensor used in initial proof of principle experimentation. The drawing is not to scale.

Before the development of the above-mentioned blended membrane, it was attempted to use a heteropoly acid, dodecamolybdophosphoric acid (DMPA) as a solid electrolyte in a gas detector and other similar applications. DMPA purchased in powder form from Alpha-Ventron was pressed at approximately 20,000 psi for about 20 seconds to form a wafer 1 inch in diameter and approximately 3 mm thick. It was necessary to use glass epoxy platens to prevent the DMPA from contacting the steel press dies in order to prevent formation of a blue liquid. Sputter deposition of platinum on the wafer to serve as catalyst was unsuccessful, first because a vacuum suitable for sputter deposition could not be obtained, apparently as a result of the water of hydration in the wafer, and then because the wafer developed cracks which made it unable to function as a gas impermeable barrier. A platinum-impregnated carbonaceous material was successfully fabricated as catalyst and electrode by placing it in the press dies and pressing it along with the DMPA. Impregnation was accomplished by adding chloroplatinic acid to carbonaceous material and decomposing to leave elemental platinum. However, use of this wafer in a gas detector (etc.) suffered from a number of drawbacks, including brittleness of the wafer and difficulty in making good electrical contact between the electrodes and DMPA. Another serious problem was that the amount of water vapor in the gas contacting the wafer had to be maintained in a narrow range to prevent deterioration of the wafer. With too much water, the wafer became spongy and with too little, it cracked. Attention was then directed toward other substances and a novel substance useful in gas detection and similar applications was discovered.

When attempting to blend an organic polymer with an inorganic compound, the usual result is to obtain a phase separation. In contradistinction to this, we have discovered that a single phase system may be obtained by admixing certain organic polymeric compounds with a heteropoly acid or salt thereof, the resulting composition of matter forming a thin film membrane which may be utilized in gas detection systems (etc.). The use of these membranes in gas detection devices (etc.) is due in some respect to the fact that heteropoly acids or salts thereof possess a high protonic conductivity, especially at room or ambient temperature. The membranes which are formed from the blend of the organic polymer and the heteropoly acid or salt thereof possess excellent transport properties as well as an increase in tensile strength over those membranes prepared from pure organic polymers. The physical properties which these thin film membranes exhibit thus provide an attractive base for their use as gas sensors (etc.). As will hereinafter be shown in greater detail, the organic-inorganic blends possess chemical, mechanical and electrical properties which indicate the two materials form a single phase system. For example, the blends possess only one glass transition temperature, which indicates a single phase system inasmuch as, if the resulting membranes were a two-phase system, or merely a physical mixture, the composition would possess two separate and distinct glass transition temperatures. In addition, the yield strength and modulus is greatly increased over those properties which are possessed by either of the two components. Another physical characteristic which indicates a single phase or true composition of matter is that the blend is transparent to visible light as well as being uniform in color.

The desired membrane comprises a blend of an organic polymer and a heteropoly acid or salt thereof, the polymer being at least partially compatible with the acid or salt. Examples of organic polymers which may be employed as one component of the blend of the present invention include poly(vinyl alcohol) (PVA), poly(vinyl fluoride), polyethylene oxide, polyethyleneimine, polyacrylic acid, polyethylene glycol, cellulose acetate, polyvinylmethylethyl ether, phenol formaldehyde resins, etc.

Examples of heteropoly acids which may be employed as the second component of the organic-inorganic blend which may be used to form a membrane will possess the generic formula:

$$A_m[X_xY_yO_z]\cdot n\ H_2O$$

in which X is selected from the group consisting of boron, aluminum, gallium, silicon, germanium, tin, phosphorus, arsenic, antimony, bismuth, selenium, tellurium, iodine, and metals of the first, second, third and fourth transitional metal series, said series including scandium, yttrium, lanthanum, actinium, titanium, zirconium, hafnium, vanadium, niobium, tantalum, chromium, molybdenum and tungsten, where Y is dissimilar from X and is selected from the group consisting of the metals of the first, second, third and fourth transitional metal series, A is selected from the group consisting of hydrogen, ammonium, sodium, potassium, lithium, rubidium, cesium, beryllium, magnesium, calcium, strontium and barium, m is an integer of from 1 to 10, y is an integer of from 6 to 12 based on x taken as 1, z is an integer of from 30 to 80 and n is an integer of from 3 to 100.

Specific examples of these compounds will include dodecamolybdophosphoric acid (DMPA), ammonium molybdophosphate, sodium molybdophosphate, potassium molybdophosphate, lithium molybdophosphate, calcium molybdophosphate, magnesium molybdophosphate, dodecatunstophosphoric acid, ammonium tungstophosphate, sodium tungstophosphate, potassium tungstophosphate, lithium tungstophosphate, calcium tungstophosphate, magnesium tungstophosphate, dodecamolybdosilicic acid, ammonium molybdosilicate, sodium molybdosilicate, potassium molybdosilicate, lithium molybdosilicate, calcium molybdosilicate, magnesium molybdosilicate, dodecamolybdogermanic acid, ammonium molybdogermanate, sodium molybdogermanate, potassium molybdogermanate, lithium molybdogermanate, calcium molybdogermanate, magnesium molybdogermanate, hexamolybdotelluric acid, ammonium molybdotellurate, sodium molybdotellurate, potassium molybdotellurate, lithium molybdotellurate, calcium molybdotellurate, magnesium molybdotellurate, dodecatungstosilicic acid, ammonium tungstosilicate, sodium tungstosilicate, potassium tungstosilicate, lithium tungstosilicate, calcium tungstosilicate, magnesium tungstosilicate, etc.

It is to be understood that the aforementioned listing of organic polymeric compounds, heteropoly acids or salts thereof are only representative of the class of compounds which may be employed in formulating the organic-inorganic blends used in the present invention.

The membranes used in the present invention are prepared by admixing the two components of the blend in a mutually miscible solvent at reaction conditions for a period of time sufficient to form the desired blend. In the preferred membrane, the mutually miscible solvent which is employed to dissolve the components comprises water, although it is contemplated that any other mutually miscible solvent, either inorganic or organic in nature may also be employed. The mixing of the two components of the membrane may be effected at reaction conditions which will include a temperature in the range of from about ambient (20°-25° C.) up to the boiling point of the mutually miscible solvent which, for example, in the case of water is 100° C. The time of reaction which is necessary to form the desired blend will vary with the particular organic polymers and heteropoly acids or salts thereof as well as the solvent and may be within a period of time ranging from about 0.5 up to about 10 hours or more in duration. Upon completion of the reaction period, the blend is cast upon a suitable casting surface which may consist of any suitable material sufficiently smooth in nature so as to provide a surface free of any defects which may cause imperfections on the surface of the membrane. Examples of suitable casting surfaces may include metals such as stainless steel, aluminum, etc., glass, polymer or ceramics. After casting the solution upon the surface, the solvent is then removed by any conventional means including natural evaporation or forced evaporation by the application of elevated temperatures whereby said solvent is evaporated and the desired membrane comprising a thin film of the polymeric blend is formed. In the preferred membrane, the polymeric blend of an organic-inorganic compound will possess a molecular weight ranging from about 2000 up to about 135,000 and preferably greater than 10,000. The thickness of the film can be controlled by the amount of polymer and heteropoly acid or salt thereof which is present in the reaction mixture or by the depth of a container in which the membrane is cast. In this respect, it is to be noted that the ratio of heteropoly acid or salt and organic polymer may vary over a relatively wide range. For example, the heteropoly acid or salt may be present in the blend in a range of from about 10% to about 70% by weight of the blend while the organic polymer may be present in an amount in the range of from about 90% to about 30% by weight of the blend. The thin film organic-inorganic blend which is prepared according to the process of the present invention will possess a thickness which may range from about 0.1 to about 500 microns.

The polymer blend membranes may be prepared by placing a predetermined amount of each of the components of the blend, namely, the organic polymer and the heteropoly acid or salt thereof, in an appropriate apparatus such as a flask. After adding the mutually miscible solvent, the mixture is allowed to remain, after thorough admixing thereof, for a predetermined period of time within the range hereinbefore set forth. As an example, poly(vinyl alcohol) and dodecamolybdophosphoric acid may be placed in a flask and dissolved in water which has been heated to 100° C. Upon completion of the desired residence time, the solution is cast upon an appropriate casting surface and the water or other solvent is removed. The desired and resulting polymer blend membrane is then recovered and utilized in an appropriate gas separation apparatus or gas sensor apparatus.

Examples of novel thin film organic-inorganic polymer blends which may be prepared include poly(vinyl alcohol)-dodecamolybdophosphoric acid, poly(vinyl fluoride)-dodecamolybdophosphoric acid, cellulose acetate-dodecamolybdophosphoric acid, polyethylene oxidedodecamolybdophosphoric acid, polyethylene glycol-dodecamolybdophosphoric acid, poly(vinyl alcohol)-dodecatungstophosphoric acid, poly(vinyl fluoride)-dodecatungstophosphoric acid, cellulose acetate-dodecatungstophosphoric acid, polyethylene oxide-dodecatungstophosphoric acid, polyethylene glycol-dodecatungstophosphoric acid, poly(vinyl alcohol)-dodecamolybdosilicic acid, poly(vinyl fluoride)-dodecamolybdosilicic acid, cellulose acetate-dodecamolybdosilicic acid, polyethylene oxidedodecamolybdosilicic acid, polyethylene glycol-dodecamolybdosilicic acid, poly(vinyl alcohol)-ammonium molybdophosphate, poly(vinyl fluoride)-ammonium molybdophosphate, cellulose acetate-ammonium molybdophosphate, polyethylene oxide-ammonium molybdophosphate, polyethylene glycol-ammonium molybdophosphate, etc. It is to be understood that the aforementioned list of polymer blends is only representative of the class of polymer blend membranes which may be prepared.

It will be helpful in gaining an understanding of the invention to examine initial proof of principle experimentation. The information presented in regard to this experimentation is not meant to limit the scope of the invention in any way.

A novel polymer blend membrane was prepared by dissolving poly(vinyl alcohol) and dodecamolybdophosphoric acid in boiling deionized water, the amount of organic polymer and heteropoly acid being sufficient to impart a 50/50 weight percent ratio to the resulting polymer blend membrane. The solution was then poured into an evaporation dish and the water was allowed to evaporate for a period of 16 hours. The resulting blended film was yellow-green in color and possessed a thickness of 20 microns.

Various analyses of the film were performed to determine whether or not the film was in single-phase or two-phase. The blended film was found to be optically transparent, and no phase separation was observed when the film was examined with an optical microscope or SEM. The specimen was also subjected to a glass transition temperature measurement inasmuch as the measurement of the glass transition temperature, or temperatures, of a polymer blend is the most commonly used criteria for determining the number of phases present in a blend. For example, a single-phase organic-inorganic blend will exhibit a single glass transition temperature between the temperatures of the components, while in a two-phase system, two separate temperatures will result. Poly(vinyl alcohol) has a known glass transition temperature of about 71° C., while the melting point temperature of dodecamolybdophosphoric acid is about 84° C. A DSC scan of the film prepared according to the above paragraphs had a peak of 78° C. while no peaks were observed at temperatures corresponding to the glass transition temperatures of poly(vinyl alcohol) or the melting point of dodecamolybdophosphoric acid.

Infrared spectroscopy of the film showed four strong bands appearing at 820 cm$^{-1}$, 885 cm$^{-1}$, 972 cm$^{-1}$, and 1075 cm$^{-1}$. The indication from this analysis is that the bands are associated with intermolecular bonding between the poly(vinyl alcohol) and the dodecamolybdophosphoric acid. In addition to these analyses, it was found that the blended film possessed increased tensile strength and modulus over that which is possessed by either poly(vinyl alcohol) or dodecamolybdophosphoric acid, the increase in tensile strength and modulus perhaps being the result of increased hydrogen bonding due to the formation of a single phase material.

The thin film membrane was cut into a disc having a 1" diameter to form membrane 1 of FIG. 1 and platinum was sputterdeposited onto both sides of the disc. The deposited platinum disc had a thickness ranging from about 100 to about 200 angstroms and a diameter of about 1.2 cm. Deposition was accomplished by means of a Hummer II sputter deposition system supplied by Technics Co. The first few attempts at platinum sputter deposition resulted in degradation of the PVA/DMPA film due to excessive electron bombardment. To reduce the flux of electrons striking the film, the biasing configuration of the sputter deposition system was changed. The addition of a biased screen between the target and film reduced the electron flux to the membrane and permitted metal to be deposited without damage. There are many alternative methods which could have been used to form the platinum deposits, such as thermal evaporation or deposition by means of an ink. The porous structure of sputter deposited catalytic agent is helpful in facilitating spillover of hydrogen ions onto the membrane, but it is not required. Note that hydrogen will migrate through solid platinum.

Referring to FIG. 1, membrane 1 was mounted in test fixture 2, which may also be referred to as a sample cell, membrane housing, or test sensor. The above mentioned platinum deposits 5 served as catalytic agent to promote dissociation and re-association or combination. Electrical contact was made to the platinum through copper platens 6, which were held in place by springs (not shown) extending between the platens and interior surfaces of the sample cell. Platens 6 did not cover the entire surface of the catalytic agent, though FIG. 1 shows this to be the case. Note that when the catalytic agent is electrically conductive and not discontinuous, electrical contact need be made only at one point. Wire leads 3 and 4 extended from the platens out of the test fixture through means for sealing against gas leakage (not shown). Leads 3 and 4 were connected to EMF and current detection means (not shown). Membrane 1 was sealed into test fixture 2 by O-rings 7 so that there were no gas leakage paths between test gas chamber 8 and reference gas chamber 9. Tubing (not shown) was connected at gas inlets 10 and 11 to provide gas flow into chambers 8 and 9 and was also connected to gas outlets 12 and 13 to conduct gas away from the chambers. Gas cylinders and gas mixing and flow control apparatus (not shown) were used to provide gas to test the sensor of fixture 2 in accordance with the herein described experiments. It must be noted that the gas mixing apparatus was capable of accuracy suitable for proof of principle experimentation but not for more rigorous work. Also, no attempt was made to separately analyze the gas mixtures prepared by diluting purchased gas.

Figure 2:
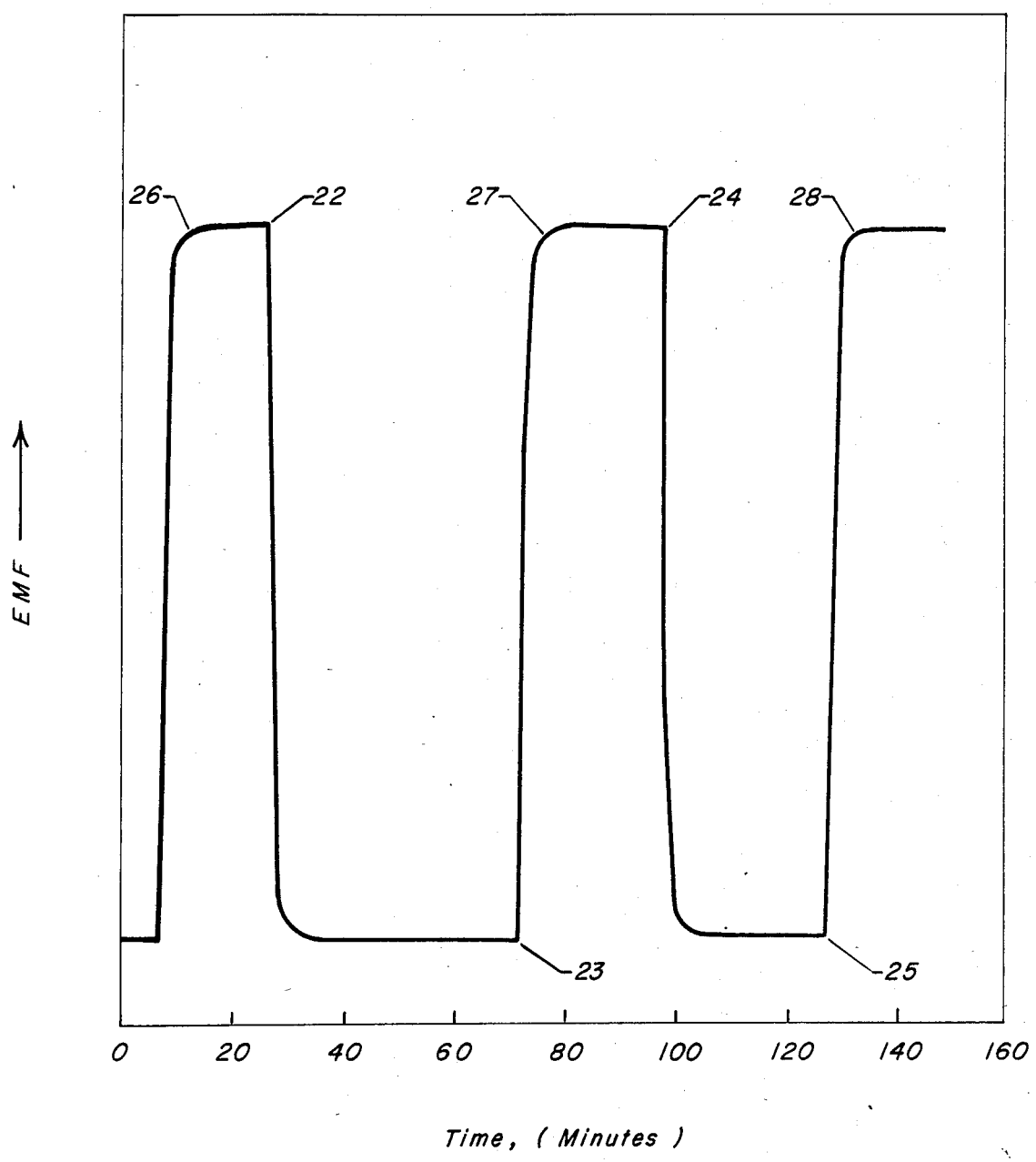
FIG. 2 depicts a portion of the results obtained when gas streams comprising hydrogen were passed through the test sensor shown in FIG. 1. It is a reproduction of the tracing of a strip chart recorder. EMF developed in the test sensor is plotted against time.

Gas flows were established through the chambers of the sample cell with both chamber pressures at essentially one atmosphere, since the chambers were vented directly to atmosphere. One flow was pure hydrogen (hydrogen partial pressure of approximately 1.0 atm.) and the other was a 2% by volume mixture of hydrogen in nitrogen (hydrogen partial pressure of approximately 0.02 atm.). The gas flows were alternated between test gas chamber 8 and reference gas chamber 9 and the voltage across wires 3 and 4 was recorded by means of a standard laboratory strip chart recorder (see FIG. 2). Referring to FIG. 2, the effect of alternating or switching the gas flows can be seen at points 22, 23, 24, and 25. The reproducibility and accuracy was very good. Voltage varied consistently between positive 49.5 millivolts and negative 49.5 mv. Response was Nernstian; the calculated voltage is also 49.5 mv (at a room temperature of 22° C.). Hydrogen flux and current flow were also determined.

Membranes having other amounts of PVA and DMPA were prepared and tested in the same manner as described above for the 50/50 weight percent blend. PVA is commercially available in several nominal molecular weights (MW). Most membranes were prepared with PVA of MW 78,000, though MW 16,000 and 133,000 were also used. Following is a tabulation of data for several membranes with varying blends by weight percent and using a reference to sample gas hydrogen pressure ratio of 100:2. Current (I) is in milliamps. Hydrogen flux is in ft.$^3$/ft.$^2$—hr. times $10^{-3}$.

| PVA/DMPA | I | Flux |
| --- | --- | --- |
| 90/10 | 0.0005 | 0.0056 |
| 75/25 | 0.031 | 0.339 |
| 50/50 | 0.1337 | 1.46 |
| 40/60 | 0.1337 | 1.46 |

The same open-circuit voltage (49.5 mv) was observed for each of the last three blends above. Reproducibility of measurements taken for the 90/10 blend was not good, leading to the conclusion that the maximum amount of PVA usable with DMPA is about 90% by weight. With DMPA contents above about 70% by weight, the membranes were brittle and also appeared to form a two-phase system.

With a PVA/DMPA membrane, it is necessary that some significant amount of water vapor be present in either the sample gas stream or the reference gas stream or both. The amount of water vapor is not critical, as it was in the case of the pressed DMPA wafer, but some is required for the detector to operate properly. In the tests performed, the smallest amount of water vapor used was that needed to cause a relative humidity of about 30% in the gas stream. It is expected that the minimum amount required is at least an order of magnitude less.

In addition to platinum, gold and palladium were deposited on membranes for use as catalytic agent. Nernstian voltage response was observed when palladium was used. Switching gas streams as described above but using a 75/25 membrane with sputter-deposited palladium yielded a strip chart record indistinguishable from that depicted by FIG. 2. Gold electrodes were ineffective; no meaningful voltage response to hydrogen partial pressure was observed. This was not unexpected, as gold, unlike platinum and palladium, does not dissociate molecular hydrogen at room temperature. It is expected that nickel will be effective as catalytic agent if it is desired to utilize the invention at higher temperatures, since nickel is known to dissociate hydrogen at higher temperatures. Other catalytic agents are available and known to those skilled in the art. The catalytic agent need not be electrically conductive; however, then the means for forming electrical connection must be in contact with the catalytic agent over a broad area, to faciliate movement of electrons from sites of the catalytic agent to the electrically conductive substance, or electrode. Areas of membrane which are not adjacent to catalytic agent are not effective in the invention. Hydrogen ions spill over from the catalytic agent to the membrane and then the protons move through the membrane.

Gases other than nitrogen were used to dilute hydrogen passed through the test sensor. Use of helium resulted in no change at all in measured voltages. The presence of small amounts of carbon monoxide (less than 5% by volume) in a 2% hydrogen (by volume) in nitrogen sample gas stream with a 100% hydrogen reference gas stream caused a change in EMF indicative of a large reduction in hydrogen partial pressure. This apparent drop in hydrogen concentration was much larger than the expected drop due to the effect of dilution of sample gas with CO. This is likely due to the competition by CO with molecular hydrogen for adsorption sites on platinum and palladium. The invention cannot be used to measure the amount of hydrogen, or other gas, present in a sample gas which also contains CO, or other substances which interfere in the same manner, unless the amount of CO, or other substance, is known by other means or constant.

In further experimentation, sample gas streams of lower hydrogen partial pressure were passed through the test sensor, the reference gas being pure hydrogen. The membrane used was 75% PVA/ 25% DMPA with palladium catalyst. Observed EMF (mv) and theoretical EMF (mv), as calculated by the Nernst equation, are as follows for several hydrogen concentrations (expressed in parts per million).

| Concentration | Observed | Theoretical |
| --- | --- | --- |
| 20,000 | 49 | 49 |
| 10,000 | 56 | 58 |
| 2,500 | 77 | 77 |
| 1,000 | 88 | 88 |

It was not possible to check lower concentrations due to limitations of the gas mixing equipment. It is believed that the value of 56 mv, above, is due to a mixture which varied from 10,000 ppm.

Response time of a sensor with a 40% PVA/60% DMPA membrane having platinum catalyst was tested. When the 100% and 2% gas streams were switched between chambers as described above, the time required for the voltage to change from 10% to 90% of its final value was approximately 6 seconds. This can be illustrated by reference to FIG. 2 and the near vertical portion of the curve at about 25 minutes and starting at point 22. The time required to trace about 80% of the length of a similar curve was about 6 seconds. It should be noted that the sample cell used is not necessarily designed for quick response.

The above description of the invention has dealt with hydrogen detection. It is obvious that any substance capable of dissociating in the presence of a catalyst to yield hydrogen ions may be detected in the same manner. An example is hydrogen chloride. The Nernst equation applies in a manner similar to that described herein. The invention is also useful in detecting any gaseous component of a gas sample which is capable of combining with hydrogen ions. Oxygen may be used to illustrate this embodiment. Protons passing through the membrane from a reference gas chamber containing pure hydrogen will combine with oxygen in a sample gas and electrons from the external circuit (for example, wires 3 and 4 of FIG. 1) to form water, in contrast to a hydrogen detector, wherein hydrogen is formed. The Nernst equation is applicable; the $E_o$ term is not O, as it is when the same substance is present on both sides of the membrane, and the partial pressure of oxygen to the one-half power times the partial pressure of hydrogen divided into the partial pressure of water replaces the analogous term of the equation. Hydrocarbons capable of hydrogenation or dehydrogenation may be subjects of detection. Examples are cyclopentadiene, benzene, isoprene, cyclohexane, and isoamylene.

As is common in many analysis instruments, the sample gas provided to a sensor may require conditioning in order to achieve effective detection. Of course, any particulate matter and liquid droplets are removed. The extent of conditioning depends on the particular gas involved and its state. For example, an extremely hot gas must be cooled to a sufficiently low temperature so as not to degrade the apparatus by melting sensor components, including the membrane. A relatively cold gas may need to be heated to a temperature which promotes a reasonable response time of the appparatus. A related factor to be considered is the necessity for knowing the temperature for use in the Nernst equation. The temperature may be measured or the temperature may be maintained at a pre-established constant value. If the calibration gas temperature is maintained at the same value, the matter is simplified. Water vapor and/or other substances are often removed from or added to a sample gas stream. Other sample-conditioning techniques may be required. For example, in a situation where the concentration of the unknown substance is extremely large and capable of saturating the apparatus, the sample may be diluted by addition of a known amount of inert gas. The actual concentration of undiluted sample can then easily be calculated.

A detector may take many forms. A portable battery-operated unit may be used as a "sniffer" to detect the presence in the atmosphere of a particular gas due to leakage from a closed system. A detector may be permanently mounted in a particular location to detect leaks. When conditioning is not required, a detector may be fabricated for insertion directly into a process pipeline. When a gas sample must be conditioned, a small sidestream may be withdrawn from a process pipeline on a continuous or intermittent basis and passed through a sample gas chamber. A quantity of reference gas may be sealed into a reference gas chamber instead of providing a continuous flow.

Figure 4:
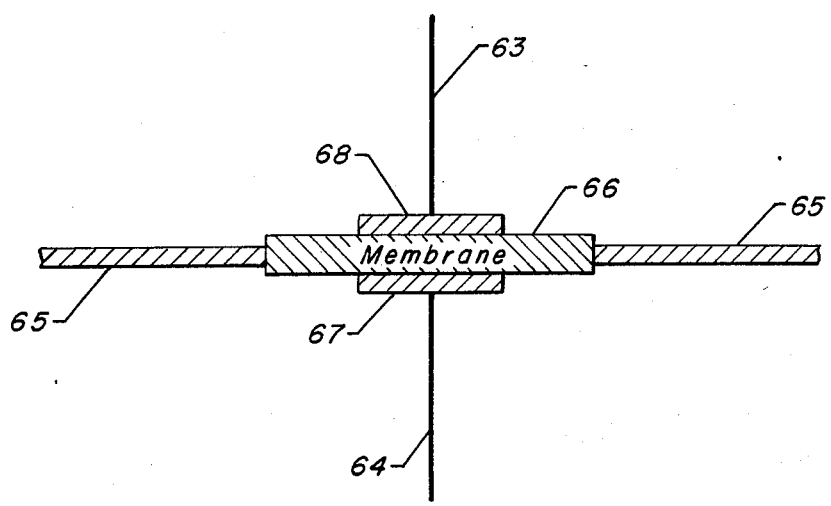
FIG. 4 depicts an embodiment of the invention, in a sectional view, in which a membrane is part of a partition separating a sample gas chamber from a reference gas chamber.

As used herein, the term "detection" includes not only sensing presence or absence of the detected substance, but measurement of the amount of substance present, either in order of magnitude or exact amounts. Gas sample refers to any portion of a gas which is the subject of detection. A gas sample may have only one component. Sample cell or membrane housing or test fixture refers to a housing or fixture which holds an electrolyte element and other required components. FIG. 4 depicts a membrane housing. Sensor is a general term denoting sensing apparatus, such apparatus comprising a membrane housing. Membrane or electrolyte element refers to an ion conducting substance suitable for use as an electrolyte in the concentration cell of this invention which has been formed into a particular physical entity, either with or without additional substances, for use in the invention. Where an electrolyte element surface is referred to as in common with a gas or gas chamber, the meaning is the same as exposed to a gas or gas chamber and such reference does not preclude the presence of catalytic agent and electrodes at or covering the surface. Gas may diffuse through covering material. Sample gas chamber refers to any space in which gas which is the subject of detection exists. For example, a sample cell can form a part of a pipeline wall such that the gas flowing in the pipeline is the sample gas and the pipeline is the sample gas chamber. The term "gas" is used herein to include vaporized liquids regardless of boiling point characteristics of the substance. As used herein, miscible means capable of being mixed where there may only be a very small degree of solubility.

Figure 3:
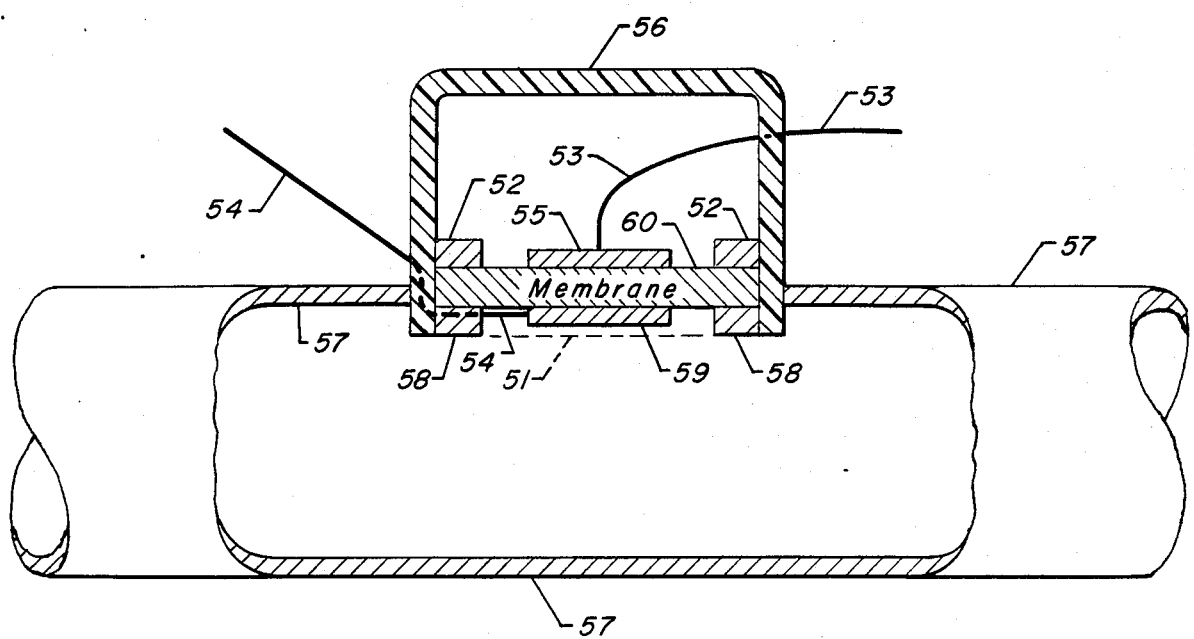
FIG. 3 depicts, in a sectional view, a sensor with a sealed reference chamber mounted on a pipeline. It is not to scale and has non-essential elements omitted.

The design of sample cells, or detectors, or membrane housings, is well known. Many configurations are possible; FIG. 1 provides an example of one type. FIG. 3 depicts an embodiment of the invention where membrane housing 56 is mounted (attachment means not shown) in the wall of pipeline 57. Gas may or may not be flowing in the pipeline. The sample gas chamber is the interior of the pipe adjacent to housing 56, while the reference gas chamber is defined by housing 56 and solid electrolyte membrane 60. Reference gas is sealed into the reference gas chamber; thus it is necessary to replace the reference gas at intervals upon its changing in concentration sufficiently to affect sensor results. Electrically conductive catalytic agent is present on both sides of membrane 60, as shown by reference numbers 55 and 59. Wire leads 53 and 54 extend outside the apparatus for connection to voltage detection means. Retaining rings 52 and 58 serve to hold membrane 60 in place at its perimeter (exact detail not shown). Screen 51 is provided to protect membrane 60 from the impact of large particles or objects. If a greater membrane surface area than that of FIG. 3 is desired, a detector may be fabricated in the form of a cylindrical probe for insertion into a pipeline. Membrane material may be placed over a perforated pipe which is sealed at one end. The interior of the perforated pipe is the reference gas chamber. It may be desirable to protect the membrane and catalytic agent by covering it with a porous substance through which sample gas can pass.

Referring to FIG. 4, an embodiment of the invention in which a membrane 66 serves as a part of partition 65 is shown. Partition 65 separates a sample gas chamber from a reference gas chamber. Catalytic agent 67 and 68 and wire leads 63 and 64 perform the functions discussed above.

What is claimed is:

1. Apparatus for detection, in a gas sample, of a gaseous component which is capable, in the presence of a catalytic agent, of dissociating to yield hydrogen ions or of combining with hydrogen ions comprising:
   (a) a thin film membrane which comprises a single phase blend of (i) from about 10% to about 70% by weight of a compound selected from the group consisting of heteropoly acids and salts thereof, where said heteropoly acids have the generic formula:

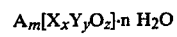

$A_m[X_xY_yO_z] \cdot n\ H_2O$ in which x is selected from the group consisting of boron, aluminum, gallium, silicon, germanium, tin, phosphorus, arsenic, antimony, bismuth, selenium, tellurium, iodine, and metals of the first, second, third and fourth transitional metal series of the periodic Table, said series including scandium, yttrium, lanthanum, actinium, titanium, zirconium, hafnium, vanadium, niobium, tantalum, chromium, molybdenum and tungsten, where Y is dissimilar from X and is selected from the group consisting of the metals of the first, second, third, and fourth transitional metal series of the periodic Table, A is selected from the group consisting of hydrogen, ammonium, sodium, potassium, lithium, rubidium, cesium, beryllium, magnesium, calcium, strontium and barium, m is an integer of from 1 to 10, y is an integer of from 6 to 12 based on x taken as 1, z is an integer of from 30 to 80, and n is an integer of from 3 to 100, and (ii) from about 90% to about 30% by weight of a polymer compatible with said compound which is selected from the group consisting of poly(vinyl alcohol), poly(vinyl fluoride), polyethylene oxide, polyethyleneimine, polyacryclic acid, polyethylene glycol, cellulose acetate, polyvinylmethylethyl ether, and phenol formaldehyde resins;

(b) a membrane housing comprising a sample gas chamber and a reference gas chamber separated by a substantially imporous partition comprising said membrane, said membrane having a first surface in common with the sample gas chamber and a second surface in common with the reference gas chamber;

(c) two separate portions of catalytic agent effective to promote dissociation and combination, one portion in contact with said first surface and one portion in contact with said second surface of said membrane;

(d) means for forming electrical connection in operative contact with said catalytic agent at said first surface and with said catalytic agent at said second surface;

(e) means for measuring EMF between said first and second surfaces;

(f) means to supply sample gas to said sample gas chamber; and (g) means to provide an indication of the presence of hydrogen or of a gas capable of combining with hydrogen ions based on the measured EMF.

2. The apparatus of claim 1 further characterized in that said catalytic agent is selected from a group consisting of platinum, nickel, palladium, and alloys thereof.

3. The apparatus of claim 1 further characterized in that said catalytic agent is electrically conductive.

4. The apparatus of claim 1 further characterized in that said catalytic agent is porous to said gaseous component.

5. The apparatus of claim 1 further including means to adjust the operating temperature of said membrane housing.

6. The apparatus of claim 1 further including means to supply sample gas to the sample gas chamber and reference gas to the reference gas chamber.

7. The apparatus of claim 1 further including means to convert said EMF measurement to concentration.

8. The apparatus as set forth in claim 1 in which said acid or salt is present in said blend in an amount in the range of from about 30% to about 60% by weight of said blend.

9. The apparatus as set forth in claim 1 in which said polymer is present in said blend in an amount in the range of from about 70% to about 40% by weight of said blend.

10. The apparatus as set forth in claim 1 in which said membrane possesses a thickness of from about 0.1 to about 500 microns.

11. The apparatus as set forth in claim 1 in which said polymer comprises poly(vinyl alcohol) and said heteropoly acid comprises dodecamolybdophosphoric acid.

12. The apparatus as set forth in claim 1 in which said polymer comprises poly(vinyl alcohol) and said heteropoly acid comprises dodecamolybdophosphoric acid, where each is present in an amount of about 50% by weight.

13. A method of detecting, in a gas sample, a gaseous component capable, in the presence of a catalytic agent, of dissociating to yield hydrogen ions or of combining with hydrogen ions, said method comprises:

(a) contacting said gas sample with a first surface of an imporous membrane comprising a solution blend of: (i) from about 10% to about 70% by weight of a heteropoly acid and salts thereof having the generic formula:

$$A_m[X_xY_yO_z] \cdot n\ H_2O$$

in which X is selected from the group consisting of boron, aluminum, gallium, silicon, germanium, tin, phosphorus, arsenic, antimony, bismuth, selenium, tellurium, iodine, and metals of the first, second, third and fourth transitional metal series of the Periodic Table, said series including scandium, yttrium, lanthanum, actinium, titanium, zirconium, hafnium, vanadium, niobium, tantalum, chromium, molybdenum and tungsten, and where Y is dissimilar from X and is selected from the group consisting of themetals of the first, second, third and fourth transitional metal series of the Periodic Table, A is selected from the group consisting of hydrogen, ammonium, sodium, potassium, lithium, rubidium, cesium, beryllium, magnesium, calcium, strontium and barium, m is an integer of from about 1 to 10, y is an integer of from 6 to 12 based on x being equal to 1, z is an integer of from 30 to 80 and n is an integer of from 3 to 100 and (ii) from about 90% to about 30% by weight of a polymer compatible with said compound selected from the group consisting of poly(vinyl alcohol), poly(vinyl fluoride), polyethylene oxide, polyethyleneimine, polyacrylic acid, polyethylene glycol, cellulose acetate, polyvinylmethyethyl ether and phenol formaldehyde resins having a first portion of catalytic agent in contact therewith effective to promote dissociation and combination;

(b) contacting a reference gas which exhibits a substantially constant known hydrogen partial pressure with a second surface of said membrane having a second portion of catalyst in contact therewith, said membrane isolating said gas sample from said reference gas; and, (c) detecting EMF between means for forming electrical connection in operative contact with said first portion of catalytic agent at said first surface and with said second portion of catalytic agent at said second surface of said membrane.

14. The method of claim 13 further characterized in that said gaseous component is elemental hydrogen.

15. The method of claim 13 further characterized in that said gaseous component is elemental oxygen.

16. The method of claim 13 further characterized in that water is added to said gas sample and/or said reference gas before the gas contacts said membrane.

17. The method of claim 13 further characterized in that the concentration of said gaseous component in the gas sample is adjusted before the sample contacts said membrane.

18. The method of claim 13 further characterized in that the temperature of said gas sample and/or said reference gas is adjusted before said gas contacts said membrane.

* * * * *